(12) United States Patent
Harper

(10) Patent No.: US 7,179,355 B2
(45) Date of Patent: Feb. 20, 2007

(54) ELECTROCHEMICAL CELL

(75) Inventor: John Christopher Harper, Saffron Walden (GB)

(73) Assignee: Alphasense Limited, Essex (GB)

( * ) Notice: Subject to any disclaimer, the term of this patent is extended or adjusted under 35 U.S.C. 154(b) by 506 days.

(21) Appl. No.: 10/369,350

(22) Filed: Feb. 19, 2003

(65) Prior Publication Data
US 2003/0209442 A1 Nov. 13, 2003

(30) Foreign Application Priority Data
Feb. 19, 2002 (GB) ................. 0203860.2

(51) Int. Cl.
*G01N 27/26* (2006.01)
(52) U.S. Cl. ............ 204/431; 204/432; 204/433; 702/24
(58) Field of Classification Search ............ 702/22, 702/24; 204/431, 432, 433
See application file for complete search history.

(56) References Cited

U.S. PATENT DOCUMENTS

| | | | |
|---|---|---|---|
| 4,325,912 A | * | 4/1982 | Sawa et al. ............ 422/95 |
| 4,478,704 A | | 10/1984 | Miyoshi et al. ............ 204/412 |
| 4,681,115 A | | 7/1987 | Holscher ............ 128/635 |
| 4,775,456 A | | 10/1988 | Shah et al. ............ 204/412 |
| 4,874,500 A | * | 10/1989 | Madou et al. ............ 204/412 |
| 5,635,627 A | | 6/1997 | Bytyn ............ 73/31.05 |

FOREIGN PATENT DOCUMENTS

| | | |
|---|---|---|
| EP | 0 126 623 | 5/1984 |
| EP | 1 154 267 | 11/2001 |
| WO | WO 96/04550 | 2/1996 |

OTHER PUBLICATIONS

Jambunathan et al., Scanning electrochemical microscopy of hydrogen electro-oxidation. Rate constant measurements and carbon monoxide poisoning on platinum, Journal of Electroanalytical Chemistry, vol. 500, 2001, pp. 279-289.*
James, S.D. "Multilayer Oxide Films on Anodized Platinum". Journal of the Electrochemical Society. Aug. 1969. vol. 116. No. 12. pp. 1681-1688.
C.E.W. Hahn et al., "A sandwich electrode for multi-gas analysis: a prototype," British Journal of Anaesth., vol. 54, Issue 6, 1982, pp. 681-687.

* cited by examiner

*Primary Examiner*—Nam Nguyen
*Assistant Examiner*—Anthony Fick
(74) *Attorney, Agent, or Firm*—Mayer & Williams PC; Karin L. Williams, Esq.

(57) ABSTRACT

Disclosed is an electrochemical sensor for measuring carbon monoxide in a gas sample, the sensor comprising a working electrode including a working electrode catalyst, and a diffusion restriction means for restricting the diffusion of the gas sample to the working electrode; wherein the working electrode catalyst comprises oxidised platinum having a hydrogen cross-sensitivity of less than 10% and being present in an amount such that the activity capacity is at least 5.

11 Claims, 5 Drawing Sheets

ELECTROCHEMICAL CELL

FIELD OF THE INVENTION

The invention relates to the field of electrochemical cells; in particular, an electrochemical cell useable as a sensor for measuring carbon monoxide in a gas sample, and a method for designing the same.

BACKGROUND OF THE INVENTION

Electrochemical sensors for the measurement of carbon monoxide in a gas sample are well known. Working, counter and reference electrodes are connected through a potentiostat circuit, which maintains a bias potential between the working and reference electrodes. The working electrode catalyses the oxidation of carbon monoxide. For a carbon monoxide sensor, the following reaction is catalysed at a platinum working electrode:

$$2CO+2H_2O \rightarrow 2CO_2+4H^++4e^-$$

A counterbalancing reduction takes place at the counter electrode. This is typically the reduction of oxygen:

$$O_2+4H^++4e^- \rightarrow 2H_2O$$

but may also be the formation of hydrogen:

$$4H^++4e^- \rightarrow 2H_2$$

The reference electrode assists in regulating the electrochemical reaction at the working electrode by providing a fixed potential.

As the number of electrons released at the working electrode, and so the working electrode current, is proportional to the amount of carbon monoxide that is oxidised, the working electrode current forms a signal which is proportional to the concentration of carbon monoxide in the gas sample.

For the proportional relationship between current and carbon monoxide concentration to apply, the sensor needs to be configured so that the reaction of carbon monoxide at the working electrode is controlled by the diffusion of the carbon monoxide to the working electrode surface. In order that the output current be diffusion controlled, two important conditions are (a) that there is a means for restricting the diffusion of the gas sample to the working electrode, typically in the form of a so-called capillary hole in the sensor casing; and (b) that an appropriate potential difference be applied between the working electrode and the reference electrode. Conveniently, setting a zero potential difference between working and reference electrodes is within the diffusion limited region, under standard conditions, although bias potentials are known to have been used in some carbon monoxide sensors.

In many of the circumstances in which carbon monoxide sensors are used, there may be other gases present which can also create a working electrode current indistinguishable from that due to carbon monoxide oxidation. These gases are known as interferents. There are several mechanisms by which an interferent can act. A gas may act as an interferent simply because it can also react at the working electrode at the bias potential in use. Alternatively, the interferent may react at the reference and/or counter electrodes, and may even be produced as a by-product of the function of the sensor itself; for example, hydrogen molecules may be evolved at the counter electrode under some conditions. Common interferents include hydrogen, alkenes and dihydrogen sulfide. The present invention primarily considers hydrogen interference, although the principles apply to other interferents. Interference can be quantified in the form of the cross sensitivity, defined below.

An important use for carbon monoxide sensors is in flue gas monitoring for monitoring completeness of combustion. In such circumstances, interference by hydrogen is common. Sensors for use in flue gas monitoring therefore need to have low hydrogen cross sensitivity. One relevant standard for flue gas monitoring sensors is the German Standard for the self-test of carbon monoxide measuring instruments for gas fixed appliances, released Aug. 5, 1988 (TÜV standard). The performance requirements dictated by TÜV for a carbon monoxide sensor include the following:

1. The sensors must respond linearly in the range 0 to 2000 ppm carbon monoxide from 10 to 30° C. with a maximum permissible error of ±5%.
2. The total error including hydrogen response must not exceed ±5% of the absolute output in a gas sample comprising 800 ppm hydrogen and 950 ppm carbon monoxide.
3. This performance must be achieved at 10° C., 20° C. and 30° C., in low oxygen environments.

It can therefore be seen that multiple parameters must be considered when designing an appropriate electrochemical sensor. The combination of a wide linear range and a low hydrogen cross sensitivity, alongside other commercial considerations such as cost and compatibility with existing equipment present a design challenge.

There have been many different approaches to solving the problem of providing a carbon monoxide sensor with a low hydrogen cross sensitivity. Of these, the simplest method of improving hydrogen cross sensitivity, as is well known to those skilled in the art, is to reduce the amount of catalyst on the working electrode.

The reason for this is also well known. As discussed above, carbon monoxide sensors are operated in the diffusion controlled region, with respect to carbon monoxide, and so changing the amount of catalyst will not affect the sensor's response to carbon monoxide. However, the response to hydrogen is controlled by the rate at which the catalyst oxidises the hydrogen. Therefore, the signal due to hydrogen is a function of the number of hydrogen binding sites; ie, the amount of catalyst present. Therefore, the hydrogen signal decreases relative to the carbon monoxide signal as the amount of catalyst is reduced; ie the cross sensitivity decreases as the amount of catalyst is reduced.

Unfortunately, reducing the amount of catalyst on a conventional platinum black working electrode to a point where hydrogen cross sensitivity is below 5% means that there is so little catalyst present that the linear range of the sensor is very poor. As a result of this consequence (and the cost of platinum black) carbon monoxide sensors are sometimes designed to use the smallest amount of catalyst possible.

One method which has been used to mitigate hydrogen cross sensitivity is described in EP 0126623 (City Technology Ltd). This is a four electrode system in which two of these electrodes are working electrodes arranged in series. The first working electrode is set to a potential where it will oxidise both hydrogen and carbon monoxide; the second working electrode is not gas specific but provides an accurate reading of hydrogen remaining after removal of all of the carbon monoxide. A commercial limitation of this type of system is that the circuitry required to drive the four electrodes is different to that used for the conventional three electrode systems sold for testing most gases. Secondly, the use of four electrodes increases the difficulty of calibration and such sensors are prone to drift due to the non-equivalent changes of catalytic activity in the two working electrodes, reducing accuracy and reliability.

It is also known to provide a second working electrode in parallel to a first working electrode. In this configuration, one working electrode is sensitive to both hydrogen and carbon monoxide, and the second responds only to hydrogen. The difference between the two currents, properly scaled and calibrated gives a corrected carbon monoxide concentration. However, calibration is difficult and this four electrode system is also prone to drift.

The paper, "A sandwich electrode for multi-gas analysis: a prototype", by C. E. W. Hahn et al, Br. J. Anaesth. (1982), 54, 681, discusses a system for simultaneously measuring two or more gases in a sandwich electrode configuration in which a first, external, metallised membrane simultaneously measures and filters out a first gas and a second, internal, cathode assays a second gas.

EP 1154267 A (Alphasense Ltd) discusses the alteration of properties, such as capacitance, of the electrochemical cell so that the additional working electrode current due to hydrogen is cancelled out by the current which flows between the working electrode and counter electrode to re-establish the potential difference between the working and reference electrodes when hydrogen reacts at the reference electrode.

EP 1154267 A (Alphasense Ltd) also discloses a four electrode electrochemical cell using a reference electrode in contact with interferent and a reference electrode located so as to not be affected by interferent.

U.S. Pat. No. 5,635,627 discloses a sensor in which the hydrogen cross sensitivity is reduced by providing two layers enriched by mercury and/or mercury ions, one on the surface of the working electrode and one on the surface of the reference electrode. It is known that mercury poisons the platinum black catalyst, reducing hydrogen sensitivity.

U.S. Pat. No. 4,681,115 (Drägerwerk Aktiengesellschaft) discloses a device having an additional electrode for sensing an external electrical potential, mounted in the outer surface region of a diffusion membrane.

U.S. Pat. No. 4,478,704 (Hitachi) uses a specified configuration of electrodes and electrolyte chamber to reduce hydrogen cross sensitivity.

U.S. Pat. No. 4,775,456 (Teledyne Industries, Inc) discusses an electrochemical gas analyser having a compensation electrode which provides a compensation signal related to the concentration of gas dissolved in the bulk of an electrolyte. This compensation signal is subtracted from the analyser output signal to give the resulting reading.

Also, some workers in the field move the bias voltage, to reduce hydrogen cross-sensitivity.

WO96/04550 (Huggenberger) uses a selective membrane and catalyst to eliminate a particular interfering gas, although we are not aware of a suitable membrane for use with hydrogen.

It is known that anodisation of a platinum working electrode leads to a permanent change in the response of the electrode to carbon monoxide and hydrogen. Anodisation reduces the cross sensitivity of a platinum working electrode, but also reduces the sensitivity of the electrode to carbon monoxide. As discussed above, those skilled in the art prefer to use as little catalyst as possible, partly for reasons of cost and partly because of the well known result that hydrogen cross sensitivity increases as the amount of catalyst is increased.

However, we have discovered that a platinum working electrode, previously subjected to an oxidation process, such as anodisation, does not suffer from increased hydrogen interference as the amount of catalyst is increased markedly, at least to the extent experienced with a non-oxidised platinum working electrode. This realisation enables us to provide a sensor having an amount of catalyst which, according to the generally understood theory, should not be capable of providing the low hydrogen cross sensitivity which results.

In this specification, the term "activity capacity" is used to denote the ratio $I_o/I_e$ as measured by the following experiment, in which $I_e$ is the working electrode current of an assembled sensor, having a diffusion restriction means, minus the background working electrode current (when no carbon monoxide is present) and $I_o$ is the working electrode current of a sensor having the diffusion restriction means removed so that it is open to excess gas sample, minus the background working electrode current.

Activity capacity is to be measured with the sensor connected to a potentiostat with a zero potential bias applied between the working and reference electrodes, in a gas mixture consisting of atmospheric air with 800 ppm carbon monoxide added thereto at a temperature of 5° C., at atmospheric pressure. Activity capacity decreases with reducing temperature, and so is tested near the lowest usage temperature.

The activity capacity can be seen as a measure of the amount of usable catalytic sites available as $I_o$ depends on the number of catalytic sites where carbon monoxide can react.

The term "cross sensitivity" is used in this specification to denote the extent to which a carbon monoxide sensor is affected by hydrogen in the following experiment.

Cross sensitivity is to be measured with the sensor connected to a potentiostat with a zero potential bias applied between the working and reference electrodes and exposed separately to two different gas mixtures: the first gas mixture consisting of 2.5% oxygen in nitrogen with 800 ppm carbon monoxide added thereto, at a temperature of 40° C., at atmospheric pressure. The second gas mixture consisting of 2.5% oxygen in nitrogen with 800 ppm carbon monoxide and 800 ppm hydrogen added thereto, also at a temperature of 40° C., at atmospheric pressure. Cross sensitivity increases with increasing temperatures and so is tested near the highest usage temperature.

The cross sensitivity is defined as the working electrode current when the sensor is exposed to the second gas minus the working electrode current when the sensor is exposed to the first gas, as a percentage of the working electrode current when the sensor is exposed to the second gas. (The background current when exposed to 2.5% oxygen in nitrogen is to be subtracted from each working electrode current prior to calculating cross sensitivity.)

SUMMARY OF THE INVENTION

According to a first aspect of the present invention there is provided an electrochemical sensor for measuring carbon monoxide in a gas sample, the sensor comprising a working electrode including a working electrode catalyst, and a diffusion restriction means for restricting the diffusion of the gas sample to the working electrode; wherein the working electrode catalyst comprises oxidised platinum having a hydrogen cross sensitivity of less than 10% and being present in an amount such that the activity capacity is at least 5.

The oxidation process reduces the hydrogen cross sensitivity of the sensor. It also decreases the activity capacity of a given quantity of oxidised platinum. However, we have appreciated that this process also reduces or obviates the extent to which increasing the amount of oxidised platinum leads to a higher hydrogen cross sensitivity. The effect of reduced activity capacity can be compensated for by having a significantly larger amount of oxidised platinum than hitherto. Increasing the amount of oxidised catalyst increases the activity capacity (as defined above) and has no significant effect on hydrogen cross sensitivity.

The hydrogen cross sensitivity and the activity capacity can both be readily determined by the experiments above.

More preferably, the hydrogen cross sensitivity is less than 10%, 5%, 2.5% or 1%. Typically, the hydrogen cross sensitivity is not reduced more than is necessary for a specific application due to the concomitant effect on activity capacity.

Preferably, the activity capacity is at least 10, 15, 20, 25 or 30. However, the most preferred activity capacity will depend on the desired linear range for the sensor and the required hydrogen cross sensitivity and it is preferred not to use substantially more platinum catalyst than is required.

The sensor can therefore be designed to satisfy any reasonable combination of hydrogen cross sensitivity and activity capacity requirements.

Preferably, the oxidised platinum is particulate. Preferably, the oxidised platinum is obtainable by oxidising platinum black. More preferably, the oxidised platinum is obtained by oxidising platinum black. The working catalyst is preferably prepared by pressing platinum black (typically mixed with a binder; for example, microparticulate PTFE), onto a support. Where platinum black is pressed at the normal pressure used in the field, i.e. around 200 kg/cm$^2$, the amount of catalyst is preferably greater than 30 mg per cm$^2$ of electrode surface. More preferably, it is between 40 and 50 mg per cm$^2$ of electrode surface area, and most preferably 45 mg per cm$^2$ of electrode surface area.

Typically, the working electrode will have a diameter of 13 mm. Preferably, at least 40 mg of oxidised particulate platinum is present on such an electrode; more preferably, between 50 and 70 mg will be applied, with around 60 mg being the most preferred option.

However, platinum black (typically mixed with a binder; for example, microparticulate PTFE) is preferably pressed onto a support at less than 180 kg/cm$^2$, more preferably less than 150 kg/cm$^2$ and most preferably at around 125 kg/cm$^2$. It has been found that, surprisingly, the materials pressed at a lower pressure than is usual in the field have greater catalytic activity and so less catalyst can be used. Thus, in this case, the amount of catalyst is preferably between 7 mg and 13 mg per cm$^2$ of electrode surface area, most preferably 10 mg per cm$^2$ of electrode surface area.

The diffusion restriction means is typically a cover having a capillary hole therethrough. The surface area of the capillary is typically between 0.01% and 1% of the surface area of the working electrode, most preferably around 0.7%. For a 13 mm diameter working electrode, the capillary is typically between 0.1 and 1.5 mm diameter and preferably around 1.1 mm diameter. As with other carbon monoxide sensors the working electrode reaction is not entirely diffusion limited, but perhaps between 85% and 99% diffusion limited, with around 95% being more typical.

Typically, the counter and reference electrode catalysts will also be made from platinum, preferably particulate platinum. Preferably, the working, counter and reference electrode catalysts are made from a mixture of platinum black and microparticulate polytetrafluoroethylene (PTFE) binder, to give a porous mixture that can be sintered then pressed on to a support, in the form of a gas porous membrane, such as a PTFE sheet. Preferably the binder is a Fluon matrix (Fluon is a Trade Mark) of around 0.23 ml per cm$^2$. A possible source of platinum black is PtBO2 grade from Johnson Matthey (of Royston, United Kingdom) or fuel cell grade platinum black from PGP Industries (Shannon Industrial Estate, County Clare, Ireland).

Oxidation is preferably achieved by a process of anodisation. Anodisation may take place at a constant bias potential, but the potential is preferably pulsed. Anodisation preferably takes place between 250 and 600 mV. More preferably, anodisation takes place between 450 and 550 mV. Most preferably, anodisation is achieved by applying pulsed bias potential, alternating between 500 mV and 0 mV. Preferably, pulses of 4 hours duration, with 4 hours between each pulse are used; preferaby, for a period of around four days. However, hydrogen cross sensitivity may be monitored after anodisation, to determine whether a sensor is ready to use and further anodisation may take place if required to bring the cross sensitivity down to the required value. Constant or pulsed potentiostatic or galvanostatic anodisation may be used.

Oxidation of the platinum catalyst may be achieved by processes other than anodisation; for example, by the application of an oxidising agent, such as hydrogen peroxide. Heating in oxygen may also be used. Platinum may be oxidised prior to forming into a working electrode.

Preferably, the particulate platinum is formed into a working electrode prior to oxidation. Preferably, the working electrode is assembled into an electrochemical sensor prior to oxidation.

Preferably, the resulting electrochemical sensor conforms to the TÜV standard.

Conveniently, this electrochemical sensor can be used with existing potentiostat circuitry, as is used for other types of three electrode sensor.

The sensor can be of otherwise conventional construction and use and can conveniently be used in existing applications without modification of standard apparatus, such as potentiostats.

Applications include combustion gas testing and monitoring of enclosed spaces.

According to a second aspect of the present invention there is provided a method of anodising a platinum electrode for use as a working electrode in an electrochemical sensor for measuring carbon monoxide in a gas sample, characterised in that the anodisation is pulsed.

Preferred features are as specified above with respect to the first aspect of the invention.

According to a still further aspect of the present invention there is provided a method of designing an electrochemical sensor for measuring carbon monoxide in the presence of an interferent, comprising the steps of determining an oxidation procedure for oxidising a platinum working electrode to reduce the hydrogen cross sensitivity of a sensor containing the working electrode to below a specified value and then increasing, preferably optimising, the amount of the platinum required to give a specified carbon monoxide activity capacity.

Preferably, the platinum working electrode is formed by pressing particulate platinum (typically mixed with a binder; for example, microparticulate PTFE) onto a support, and the method of designed an electrochemical sensor includes the step of optimising the pressure at which the particulate platinum is pressed, taking into account not just the integrity of the resulting working electrode but also the amount of platinum required to give a specified carbon monoxide activity capacity at a particular electrode pressing pressure.

Preferred features are as specified above with respect to the first aspect of the invention.

BRIEF DESCRIPTION OF THE DRAWINGS

The invention will be further described, by way of illustration, with reference to the accompanying drawings, in which.

DETAILED DESCRIPTION OF AN EXAMPLE EMBODIMENT

Figure 1:
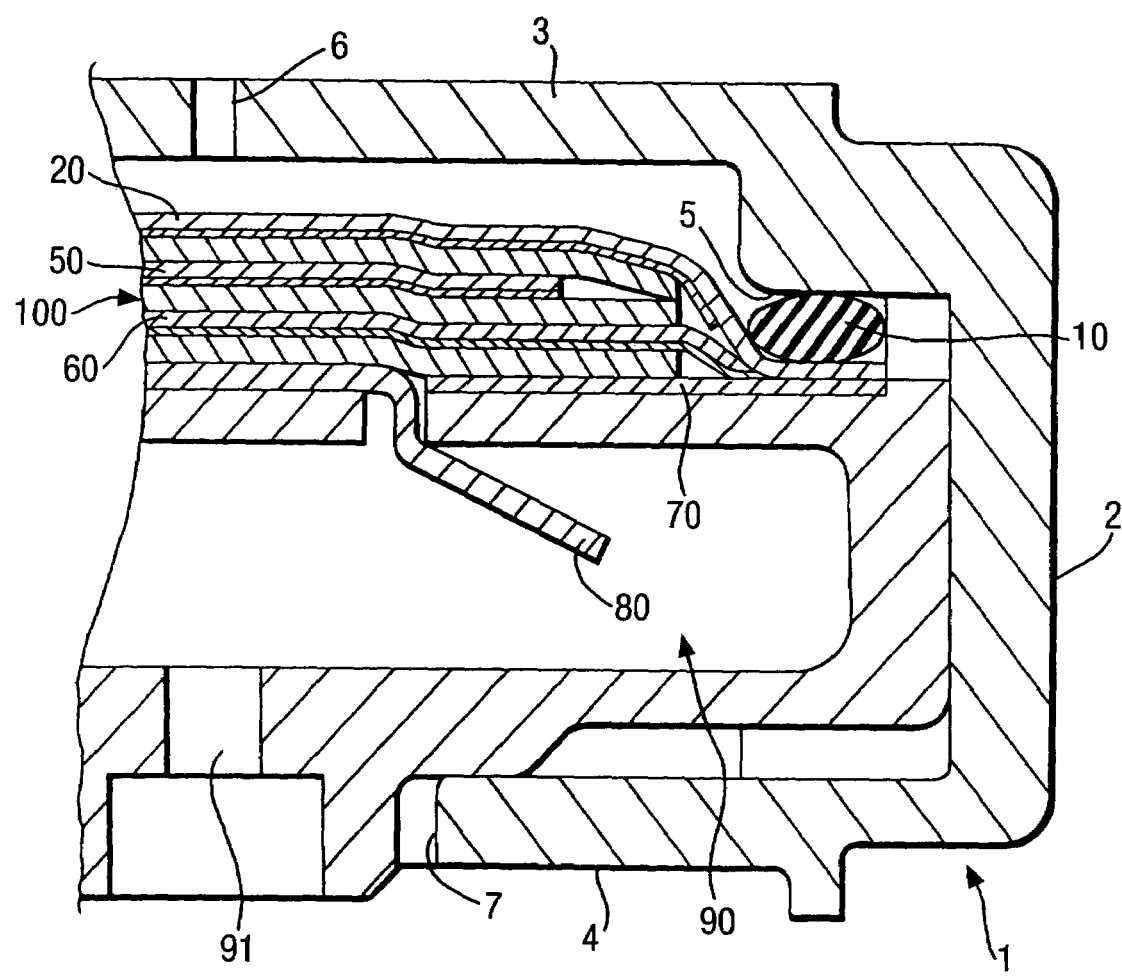
FIG. 1 is a sectional view of one embodiment of an assembled carbon monoxide sensor in accordance with the invention.
Figure 2:
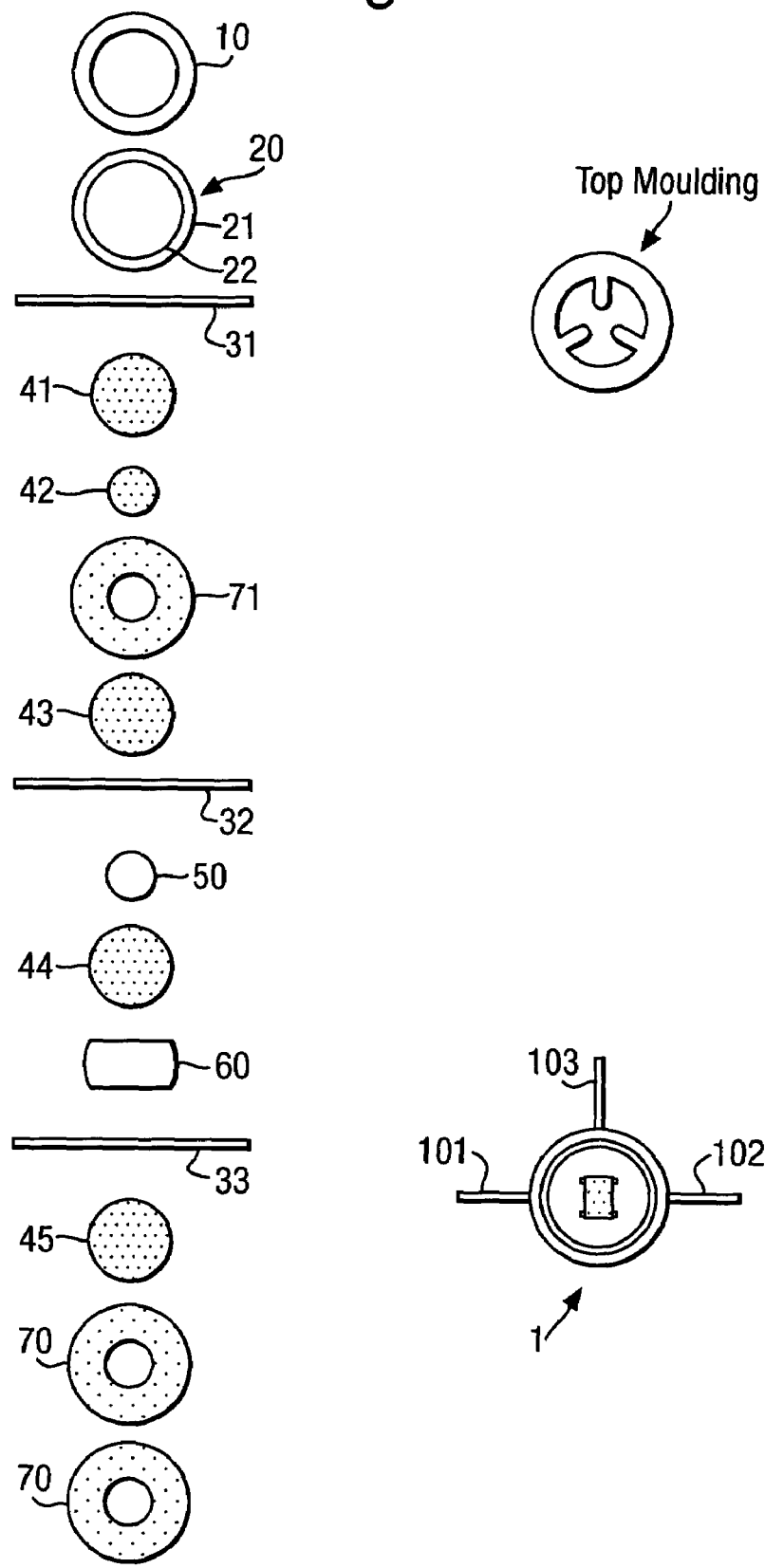
FIG. 2 is an exploded view of an electrode stack assembly for the electrochemical sensor of FIG. 1.

FIGS. 1 and 2 illustrate one preferred embodiment of a sensor in accordance with the invention for measuring carbon monoxide in a gas sample. FIG. 1 is slightly simplified, with some of the components shown in FIG. 2 omitted from FIG. 1 for clarity. The physical structure, construction and operation of the sensor are generally known. The novelty lies in the working electrode, discussed below, and the resulting sensor properties.

As shown in FIG. 1, the sensor comprises a generally cylindrical sensor housing or casing 1, made of a corrosion resistant engineering plastics material such as polycarbonate or polysulfone, approximately 25 mm in diameter in which is housed an electrolyte reservoir 90 made of polysulfone or polycarbonate, an electrode stack assembly 100 and a wick 80 of unbound glass fibre, a hydrophilic non-conductive electrolyte transporting material which functions as a wick, extending into the reservoir 90 for contact with electrolyte therein.

Sensor casing 1 has a cylindrical side wall 2 and generally planar circular top and bottom walls, 3 and 4, respectively. The top wall 3 has a stepped configuration and includes an annular shoulder portion 5 around the periphery. A central circular opening 6 passes through the top wall 3 which functions to permit gas passage to the interior of the casing whilst acting as a means to restrict the diffusion of the gas sample to the working electrode, discussed below. The circular opening 6 is referred to as the capillary. In the present example, the capillary is 1.1 mm diameter. The bottom wall 4 includes a larger central circular opening 7 through which protrudes part of the reservoir 90, this part including a suitable opening 91 to enable supply of electrolyte to the reservoir, during manufacture.

The casing 1 is conveniently of two-part construction (not shown) for assembly purposes. The electrode stack 100 is further illustrated in FIG. 2. In FIG. 2, the relative dimensions of the various components are as shown. The components of the electrode stack are generally of planar or sheet-like form, generally being of circular or annular configuration as shown in FIG. 2.

Working from the bottom up as shown in FIG. 2, electrode stack 100 comprises two annular stack bases 70 of gas porous hydrophobic PTFE polymer material in the form of Zytex, Goretex or Mupor (Zytex, Goretex and Mupor are Trade Marks). (Only one stack base is shown in FIG. 1). These are followed by a circular separator disc 45 made of unbound glass fibre which is a hydrophilic, non-conductive material permeable to the electrolyte which functions to wick electrolyte. Then follows a platinum strip or rod 33 (not shown in FIG. 1) that functions as an electrical conductor for connection to a first terminal pin 101 on the sensor housing. The assembly then includes a counter electrode 60 that is generally rectangular in plan. Counter electrode 60 comprises a catalytic layer covering the full extent of the downward facing side of a hydrophobic microporous PTFE support (e.g. of Zytex, Goretex or Mupor). The catalytic layer is formed from a mixture of platinum black catalyst and PTFE binder sintered at elevated temperature to give a porous binder/catalyst material that can be bonded to the support.

The stack then includes a further separator disc 44 similar to separator disc 45. Next in the assembly is circular reference electrode 50 of similar materials and construction as the counter electrode 60 and comprising a platinum black/PTFE catalytic layer covering the downward facing side of a hydrophobic microporous PTFE support. Then follows a second platinum strip 32 similar to strip 33 and leading to a second terminal pin 102. A third separator disc 43 similar to discs 45 and 44 is then provided, followed by a further gas porous PTFE ring 71, similar to stack base 70 and having a smaller separator disc 42, which is similar to discs 43, 44 and 45 in all but size. Thereafter, a further separator disc 41, similar to disc 45 is provided followed by a third platinum strip 31, similar in construction and function to strips 33 and 32 and leading to a third terminal pin 103. (Items 71, 42 and 41 and platinum strips 31 are not shown in FIG. 1).

Finally, the electrode assembly includes a circular working electrode 20. Although formed from similar materials and construction to electrodes 60 and 50, it has undergone an anodisation procedure, discussed below. The working electrode 20 includes an anodised platinum black/PTFE catalytic layer on the circular central portion only of the downward facing surface of a hydrophobic microporous PTFE support. In the present example, the catalytic portion of the working electrode 20 is 13 mm in diameter.

The components of the electrode stack assembly are assembled in order on the reservoir 90 and wick 80 with the electrode catalytic layers on the undersides of the associated supports, facing downwardly towards the reservoir, as shown in FIG. 1. An "O" ring 10 is located on top of the assembly, being sized to contact the outer periphery of the working electrode support 21. On insertion of the assembly into the casing 1, as shown in FIG. 1, the casing shoulder 5 contacts the "O" ring 10 which urges the working electrode support 21 into contact with the outer periphery of the stack base 70 and forms a seal, also bringing the various electrode stack components into close contact as shown. During this assembly some of the electrode stack components deform from their initially planar condition, but such components are still to be considered as of planar configuration.

5 Molar sulfuric acid electrolyte is located in the chamber within reservoir 90 for contact with wick 80. The reservoir is not filled completely with electrolyte, leaving a free volume in the reservoir to allow for the possibility of water absorption resulting in an increase in the electrolyte volume, or for water loss through evaporation past the working electrode 20, reducing electrolyte volume. The reservoir may include hydrophilic non-conductive wicking or wetting material to provide a continuous electrolyte path from the reservoir to the separator discs.

The electrode supports are all made from hydrophobic microporous PTFE. The stack base 70 is made from PTFE. The hydrophobic properties of the material mean it is impermeable to the electrolyte so that electrolyte is effectively sealed within the housing by virtue of the seal between stack base 70 and the working electrode support 21 produced by "O" ring 10.

Before use, the sensor is assembled, the working electrode is anodised, and then the sensor is stabilised, tested and calibrated. In each of these steps, the casing terminal pins are connected to an external potentiostat, which is used in known manner to set the potential difference of the working electrode with respect to the potential of the reference electrode.

Figure 3:
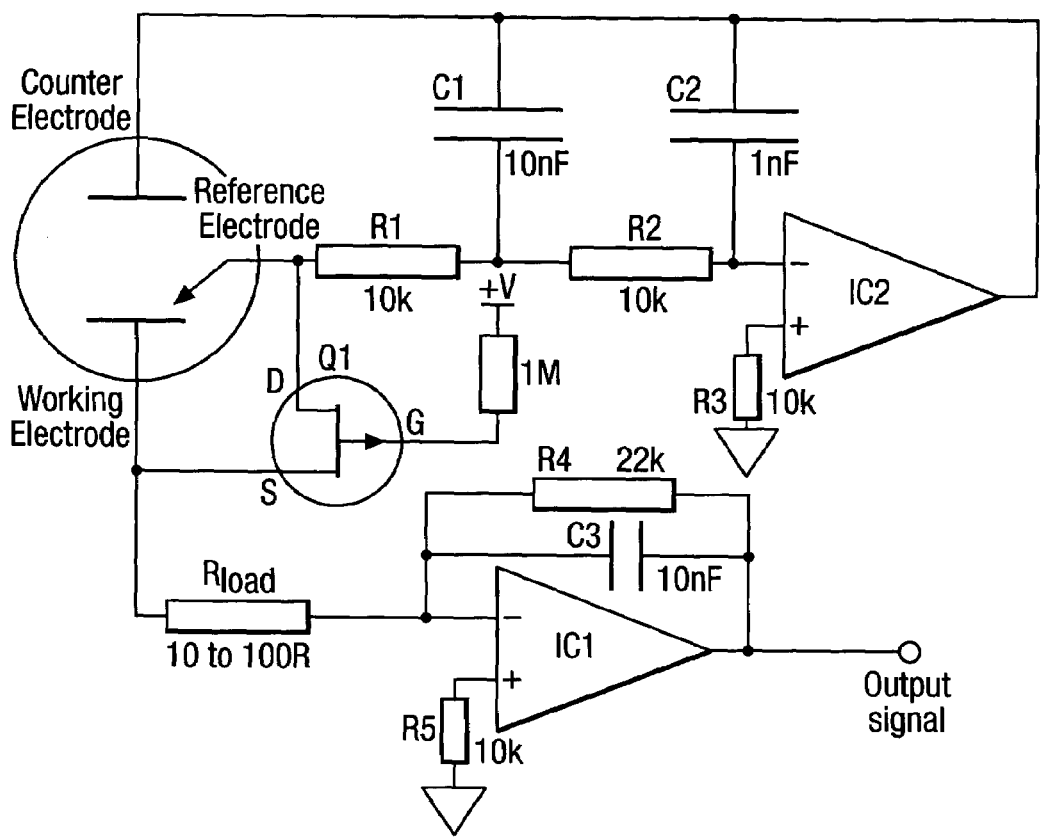
FIG. 3 is a circuit diagram of a standard potentiostatic circuit, suitable for use with the electrochemical sensor of the present invention.
Figure 4:
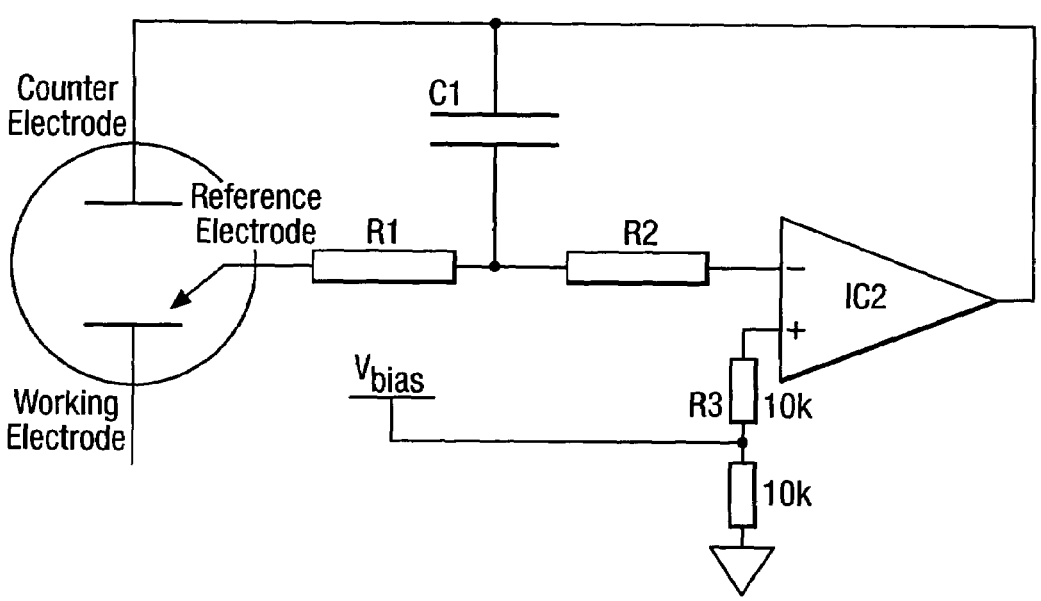
FIG. 4 is a variant of part of the circuit diagram of FIG. 3, for applying a bias potential between the working and reference electrode of a carbon monoxide sensor.

An example potentiostat circuit which can be used to operate the electrochemical sensor of the present invention is shown in FIG. 3. The reference electrode provides a standard voltage which, in a potentiostatic circuit, sets the working electrode operating potential. An important benefit of the invention is that this potentiostat circuit is a well-known standard, which can readily be optimised by one skilled in the art. FIG. 4 illustrates a conventional modification which enables a bias potential to be applied between the working and reference electrodes. In FIGS. 3 and 4, IC1 and IC2 are Operational Amplifiers, and Q1 is a depletion mode JFET. Application note AAN 105, available from Alphasense Limited (Great Dunmow, United Kingdom) discusses such circuitry in more depth.

Working electrode 20 according to the present invention can be prepared in the following way. Firstly, 1.0 g of platinum black catalyst is added to a 1.8 ml solution of 1.4% isooctylphenoxypolyethoxyenthanol (Triton X) solution in water. Thereafter, 0.15 ml of PTFE in aqueous dispersion (Fluon GP1 brand) is added thereto and the components are mixed by sonication (10 minutes) and stirred with a magnetic stirrer bar.

Appropriate platinum black catalyst is available from Johnson Matthey plc, (PtBO2 grade platinum black with typical particle size 0.3 µm). Platinum black is a particulate mixture of platinum and platinum oxide. Triton X is available from BDH (Poole, United Kingdom) and Fluon GP1 is distributed by Whitford Plastics Ltd., Runcorn, United Kingdom. (Triton X and Fluon are Trade Marks).

The resulting slurry is then drawn up into a pipette, and 120 microlitres is dispensed in to a circular depression on an electrode forming mould. The mould comprises disc shaped depressions of 13 mm diameter over a pressable member. The catalyst is spread throughout the disc with the pipette, as evenly as possible.

The resulting cakes of catalyst are then dried for 60 minutes at 60° C., followed by a further 30 minutes at 150° C., then 15 minutes at 280° C. A membrane disc, of gas porous hydrophobic PTFE, such as Zytex, Goretex or Mupor (Zytex, Goretex and Mupor are Trade Marks) is placed on top of the press. A baked catalyst disc from the previous step is then placed on top of the membrane, with the cake side facing down, and the catalyst cake and electrode disc being lined up coaxially. Next, a mechanical press applies pressure to the pressable member, thereby pressing the catalyst into the PTFE membrane. Thereafter, the press can be removed revealing the catalyst cake.

By choosing an appropriate size of catalyst cake and size and shape of PTFE membrane, this procedure, up to this stage, can be adapted to make counter and reference electrodes.

The working electrodes are then used to form electrochemical sensors according to the construction of FIGS. 1 and 2, as discussed above. Next, the working electrodes are oxidised, by means of an anodisation procedure.

Using a potentiostat circuit, according to FIGS. 3 and 4, a pulsed potential difference is applied to the working electrode. A potential of 500 mV is applied to the working electrode, relative to a platinum black reference electrode, in air, for 4 hours. Thereafter, the potential difference is reduced to zero for 4 hours. This pulse is repeated until cross sensitivity is below the required value. 12 pulses (4 days) were used for the examples herein. The sensitivity of the sensor to carbon monoxide and so its activity capacity is also reduced, but to a lesser extent Thereafter, prior to use, the sensors are stabilised, by connecting them to a potentiostatic circuit with a zero bias between the working and reference electrodes, in air. The working electrode current is monitored; once it has become stable, the sensors can be further tested, for example as described in U.S. patent application Ser. No. 09/909,131 to Alphasense Limited.

In use, a potentiostat applies a zero potential difference between the reference and working electrodes, with the resulting working electrode current being proportional to the concentration of carbon monoxide up to over 2000 ppm. Carbon monoxide is oxidised at the working electrode whilst oxygen is reduced at the counter electrode to balance the electrochemical reaction taking place at the working electrode.

Before use in practical applications, however, the individual electrochemical sensor should be tested for its performance. This can be achieved by exposing the sensor to a known concentration of carbon monoxide, for example, 800 ppm carbon monoxide, and measuring the resulting working electrode current. Due to the linear nature of the output from this type of sensor, only one calibration point is required. The activity capacity of the sensor can also be measured, by the procedure discussed above.

Figure 5A:
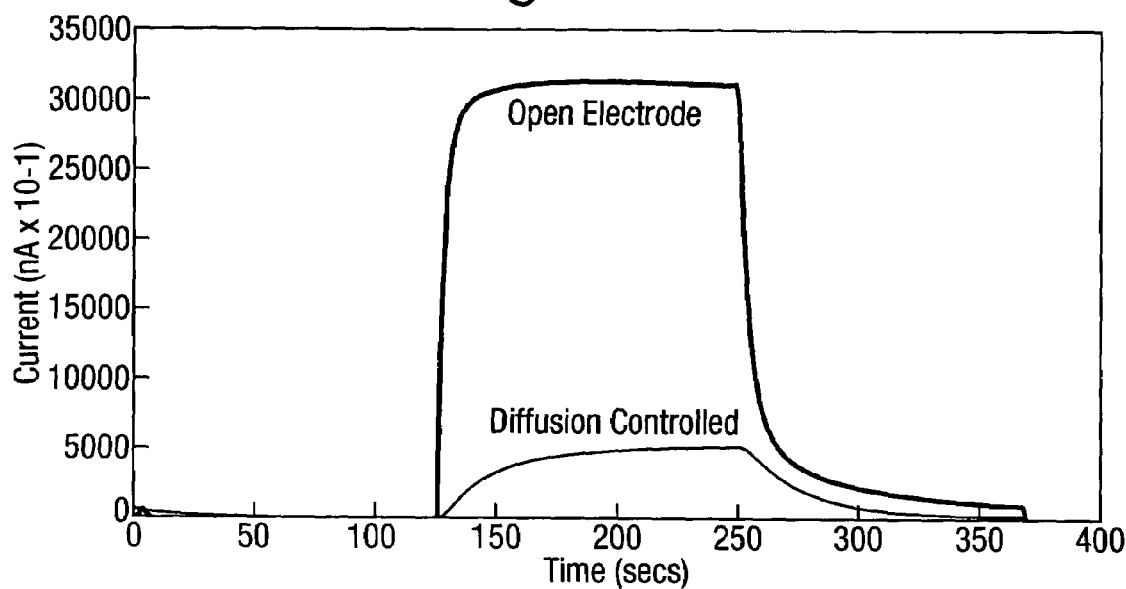
FIG. 5 is two graphs of current (nA) in time (secs) showing the response to 800 ppm carbon monoxide of diffusion limited and activity limited electrochemical sensors at 5° C. for (5a) a sensor with much increased loading, as per the present invention and (5b) a sensor with typical platinum loading.
Figure 5B:
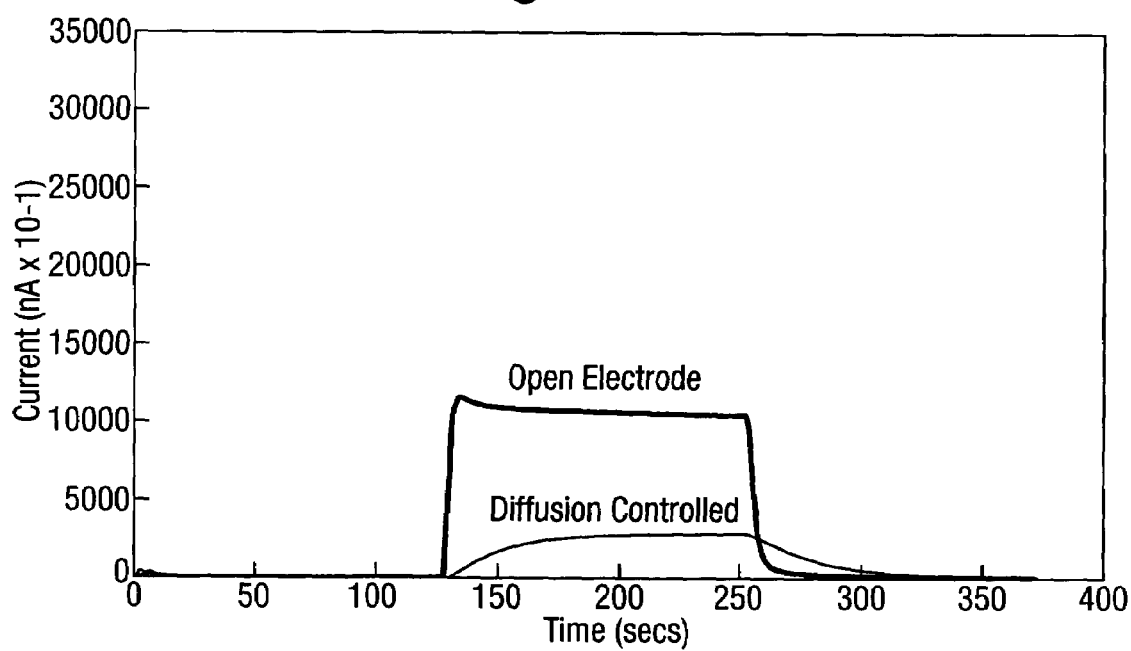

FIG. 5$a$ shows the current response (nA×$10^{-1}$) with time (secs) for a sensor manfactured as above, with a catalyst loading of 60 mg of anodised platinum black on a 13 mm diameter disc (45 mg per $cm^2$) with the sensor exposed to atmosphere air and then atmospheric air with 800 ppm carbon monoxide, at 5° C. and atmospheric pressure. The response of diffusion controlled (1.1 mm diameter capillary present) and open electrodes are shown. It can be seen that the activity capacity is 31300/500=6.26. FIG. 5$b$ shows the response of an anodised carbon monoxide sensor with a loading of 28 mg of unanodised platinum black on a 13 mm diameter disc (21 mg per cm$^2$). This has an activity capacity of only 10580/2700=3.92.

Figure 6:
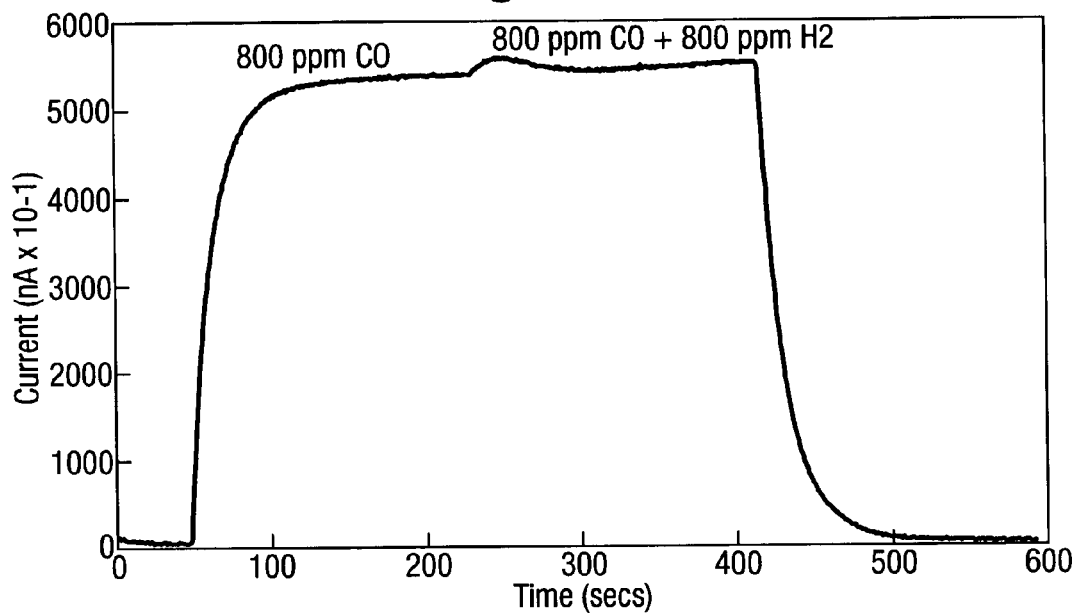
FIG. 6 is a graph of current (nA) in time (secs) showing the response to 800 ppm carbon monoxide and then 800 ppm carbon monoxide plus 800 ppm hydrogen at 40° C. of an electrochemical sensor according to the present invention.

FIG. 6 shows the current response (nA×10$^{-1}$) with time (secs) for a sensor manufactured as above, with a catalyst loading of 60 mg of anodised platinum black on a 13 mm diameter disc (45 mg per cm$^2$) exposed to 800 ppm carbon monoxide then 800 ppm carbon monoxide plus 800 ppm hydrogen (both in nitrogen with 2.5% oxygen, at 40° C., atmospheric pressure). It can be seen from the result that the cross sensitivity, as defined above, is approximately 120/(5475−50)=2.2%.

Figure 7:
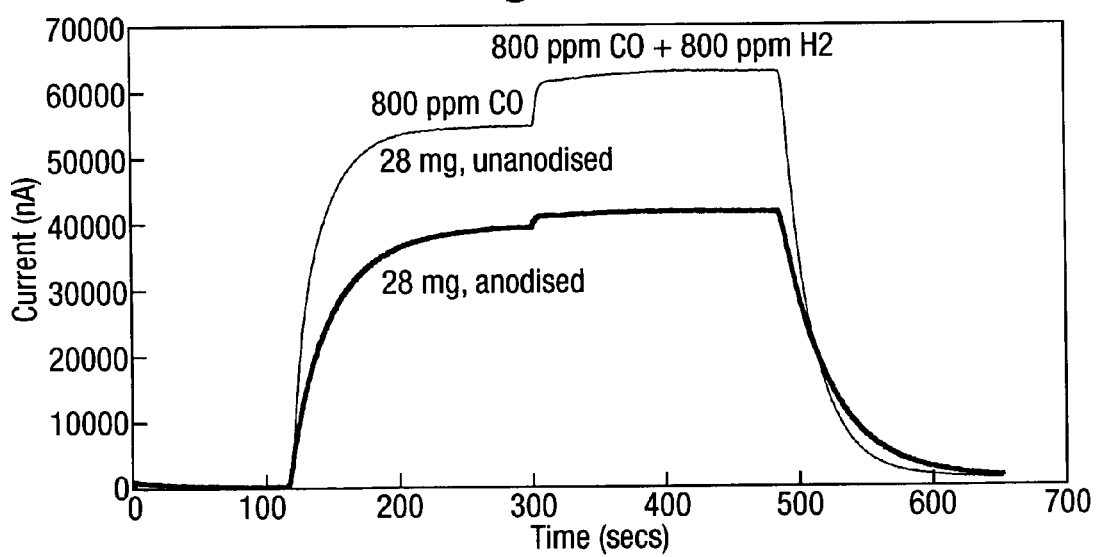
FIG. 7 is a graph of current (nA) in time (secs) showing the response to 800 ppm carbon monoxide at then 800 ppm carbon monoxide plus 800 ppm hydrogen at 5° C. of electrochemical sensors with 28 mg platinum loading for a 13 mm diameter working electrode which are unanodised (thin line) or anodised as per the process of the present invention (thick line).

FIG. 7 shows the current response (nA) with time (secs) for a sensor manufactured as above, with the working electrode both anodised (thick line) and unanodised (thin line) with a catalyst loading of only 28 mg of anodised platinum black on a 13 mm disc (21 mg per cm$^2$) exposed to 800 ppm carbon monoxide and then 800 ppm carbon monoxide plus 800 ppm hydrogen (both in nitrogen with 2.5% oxygen, at 5° C., atmospheric pressure). This graph shows the reduction in the current response to carbon monoxide for the sensor with an anodised working electrode and also shows that the interference by hydrogen is proportionally more reduced in the sensor with an anodised working electrode.

We believe that anodisation affects the hydrogen cross sensitivity of platinum working electrodes by the following mechanism. According to the reactant pair mechanism first proposed by S. Gilman, (J. Phys. Chem., 71, 1967, 4337), the catalytic oxidation of carbon monoxide requires a surface platinum oxide site adjacent to a platinum site;

$$PtO + PtCO \rightarrow CO_2 + 2Pt \quad (1)$$

In contrast, consider the mechanism of the hydrogen oxidation process proposed by Stonehart et al (P. Stonehart and P. N. Ross, Electrochim Acta, 21, 1976, 441) in which two free platinum sites are required to facilitate the dissociative adsorption of molecular hydrogen.

$$2\,Pt + H_2 \underset{k_{-1}}{\overset{k_1}{\rightleftharpoons}} 2\,Pt\text{--}H \quad (2)$$

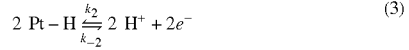

$$2\,Pt\text{--}H \underset{k_{-2}}{\overset{k_2}{\rightleftharpoons}} 2\,H^+ + 2e^- \quad (3)$$

As the surface is oxidised the ratio of sites suitable for hydrogen oxidation to sites suitable for carbon monoxide oxidation is therefore decreased, with a concomitant decrease in the response of the surface to carbon monoxide. Overanodisation leads to increased formation of higher oxides of platinum, destroying the response. The alteration in carbon monoxide and hydrogen catalysis rate with increasing oxidation is complex as anodisation alters platinum oxidation in patches rather than uniformly. We propose that pulsed anodisation leads to increased nucleation of patches of oxidised platinum.

Anodisation, or alternative oxidation procedures including thermal or chemical oxidation, may be applied to platinum black before it is formed into an electrode.

Thus, the illustrated sensor has improved hydrogen cross sensitivity compared to sensors with non-oxidised particular platinum working electrodes, whilst retaining sufficient activity capacity for key practical applications.

In the above examples, the mixture of platinum black and microparticulate PTFE binder is pressed onto the gas permeable membrane at 200 kg/cm$^2$, which is typical in the field of sensor manufacture. We have also found that, surprisingly, if the working electrode is pressed at a lower pressure than is typical in the field, then less anodised platinum black is required.

In a further example, an electrochemical sensor was made using the procedure above, except that the mixture of platinum black and microparticulate PTFE binder was pressed at 125 kg/cm$^2$ and only 30 mg of anodised platinum black was applied to a 21 mm diameter working electrode, i.e. only 10 mg/cm$^2$ of electrode surface area. Despite the use of less catalyst than in the examples above, a cross-sensitivity of less than 10% and an activity capacity of greater than 5 was achieved.

We hypothesize that by using a lower pressure to press the electrode, more active catalytic sites are available. As less platinum is required, this leads to an economic benefit.

We claim:

1. An electrochemical sensor for measuring carbon monoxide in a gas sample, the sensor comprising a working electrode including a working electrode catalyst, and a diffusion restriction means for restricting the diffusion of the gas sample to the working electrode; wherein the working electrode catalyst comprises oxidised platinum having a hydrogen cross sensitivity of less than 10% and being present in an amount such that the activity capacity is at least 5.

2. An electrochemical sensor according to claim 1, wherein the oxidised platinum is particulate.

3. An electrochemical sensor according to claim 2, wherein the oxidised platinum is obtained by oxidising platinum black.

4. An electrochemical sensor according to claim 3, in which the particulate platinum is formed into a working electrode prior to oxidisation to oxidised platinum.

5. An electrochemical sensor according to claim 4, wherein the working electrode is formed by pressing a mixture of binder and at least one material selected from the group consisting of particulate platinum and oxidised particulate platinum onto a support at a pressure of less than 180 kg/cm$^2$.

6. An electrochemical sensor according to claim 1, wherein the diffusion restriction means comprises a cover having a capillary hole therethrough, and wherein the surface area of the capillary is between 0.0 1% and 1% of the surface area of the working electrode.

7. An electrochemical sensor according to claim 1, wherein the platinum is oxidized by at least one method selected from the group consisting of (a) the application of an oxidising agent to platinum, and (b) heating of the platinum in oxygen.

8. An electrochemical sensor according to claim 1 wherein the platinum is oxidised by a process of anodisation.

9. An electrochemical sensor according to claim 8, wherein the platinum is anodised at a voltage between 250–600 mV.

10. An electrochemical sensor according to claim 8, wherein the platinum is anodised with a pulsed potential.

11. An electrochemical sensor according to claim 8, wherein the hydrogen cross-sensitivity is monitored after anodisation to determine whether the sensor is ready to use, and wherein Further anodisation takes place if it is determined that this is required to bring the cross-sensitivity down to the required value.

* * * * *